United States Patent

Wu

[11] Patent Number: 5,927,976
[45] Date of Patent: *Jul. 27, 1999

[54] MEDICATION INJECTION DEVICE AND METHOD

[75] Inventor: Gin Wu, Corte Madera, Calif.

[73] Assignee: Cyberdent, Inc., Novato, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/644,340

[22] Filed: May 10, 1996

[51] Int. Cl.[6] ................................................. A61C 1/10
[52] U.S. Cl. .............................. 433/82; 433/80; 433/84; 433/87; 604/22; 606/80
[58] Field of Search .................................. 433/82, 84, 87, 433/80; 604/22, 27, 131, 154; 606/80

[56] References Cited

U.S. PATENT DOCUMENTS

| Re. 27,923 | 2/1974 | Bentov | 128/221 |
|---|---|---|---|
| 2,442,033 | 5/1948 | Brantly et al. | 433/165 |
| 3,244,172 | 4/1966 | Brown | 128/218 |
| 3,406,685 | 10/1968 | May | 128/214.4 |
| 3,750,667 | 8/1973 | Pshenichny et al. | 128/215 |
| 4,021,920 | 5/1977 | Kirschner et al. | 433/82 |
| 4,193,197 | 3/1980 | Kuris et al. | 433/82 |
| 4,220,446 | 9/1980 | Walker | 433/87 |
| 4,356,828 | 11/1982 | Jamshidi | 128/754 |
| 4,787,893 | 11/1988 | Villette | 604/188 |
| 4,944,677 | 7/1990 | Alexandre | 433/165 |
| 4,973,247 | 11/1990 | Varnes et al. | 433/82 |
| 5,041,119 | 8/1991 | Frigg et al. | 606/96 |
| 5,085,631 | 2/1992 | Leighton | 604/28 |
| 5,201,656 | 4/1993 | Sicurelli, Jr. | 433/166 |
| 5,275,563 | 1/1994 | Cohen et al. | 433/224 |
| 5,372,583 | 12/1994 | Robert et al. | 604/51 |
| 5,409,376 | 4/1995 | Murphy | 433/29 |
| 5,429,504 | 7/1995 | Peltier et al. | 433/165 |
| 5,554,154 | 9/1996 | Rosenberg | 606/80 |

FOREIGN PATENT DOCUMENTS

| A61B 10/00 | 7/1988 | Germany . |
|---|---|---|
| 717850 | 11/1954 | United Kingdom . |
| 1430092 | 3/1976 | United Kingdom . |
| WO 89/11310 | 11/1989 | WIPO . |
| WO 96/31164 | 10/1996 | WIPO . |

OTHER PUBLICATIONS

Pearce, Jr. "Intraosseous Injection For Profound Anesthesia of The Lower Molar" (1 page).

Cannell, et al. "Intraosseous Injections Of Lignocaine Local Anaesthetics" *British Dental Journal*, vol. 141; Jul. 20, 1976; pp. 48–50.

Lilienthal "A Clinical Appraisal Of Intraosseous Dental Anesthesia", Oral Surg., vol. 39, No. 5; May 1975; pp. 692–697.

Bourke "Intra–Osseous Anesthesia" *Dent. Anesthesia And Sedation*, vol. 3, No. 2, Jul. 1974, pp. 13–18.

Dorfman "Predictable And Effective Anesthesia Utilizing Intraosseous Injections".

Leonard "The Efficacy of An Intraosseous Injection System Of Delivering Local Anesthetic".

Magnes "Intraosseous Anesthesia", Anesthesia Progress, Nov. 1968, pp. 264–267.

Garfunkel, et al. "Intraligamentary—Intraosseous Anesthesia", Int. J. Oral Surg. 1983; 12: 334–339.

Biddulph "Intraosseous Anesthesia For Dental Procedures", The Arizona Dental Journal.

*Primary Examiner*—John J. Wilson
*Attorney, Agent, or Firm*—Limbach & Limbach, LLP

[57] ABSTRACT

A medication injection method and related device with a hollow drill bit for delivery of anesthetic or other medication through the hollow drill bit are disclosed. The device preferably includes a hollow drill bit, a disposable fluid dispenser, a handpiece, a handle, and a foot control pedal. The device can deliver anesthetic or other medication before, during and/or after drilling of a tooth or bone structure without removing the drill bit. The invention relates to an intraosseous and/or hard tissue drug delivery system that combines perforating and drug delivering functions in one device and one operation.

20 Claims, 10 Drawing Sheets

MEDICATION INJECTION DEVICE AND METHOD

FIELD OF THE INVENTION

This invention relates to medical devices used to deliver medication through or into bone and other hard tissue. In particular, this invention relates to a medication injection device with a hollow drill bit having a bore where the drill is particularly useful for delivering anesthetic through the hollow drill bit before, during, or after drilling without removing the drill bit.

BACKGROUND OF THE INVENTION

Dentists often administer local anesthetic to patients to minimize pain during dental procedures. Many dentists and patients, however, are dissatisfied with the results that dentists achieve using traditional anesthetic injection techniques. Problems with administration of anesthetic include: delays between injection and effect, the long duration and extent of postoperative numbness for patients, and the occasional inability to achieve total anesthesia.

One prior art solution was the intraosseous injection technique developed in the early 1900's. The intraosseous injection technique is a 3-step procedure. First, the gingiva over a target point of perforation, (the point between the problem tooth and the adjacent tooth) is topically anesthetized. Second, a dentist drills through the cortical plate of the selected tooth to create a hole. Lastly, local anesthetic solution is injected through the hole into the cancellous bone.

The intraosseous injection technique eliminated many of the problems of the traditional injection. The anesthetic took effect quickly and efficiently and caused little postoperative numbness. In addition, unlike other techniques, it worked well in almost all patients. However, the intraosseous injection technique had many problems. In addition to being difficult to perform, the technique produced large holes causing significant bone trauma with increased risks of bone infection.

One prior art improvement of the intraosseous injection technique was the development of the Stabident System which involved the use of a drill with a small diameter (27 G hypodermic needle) drill bit. The use of the small drill bit reduced tissue damage and the risk of infection.

In spite of these advantages, the Stabident System had several drawbacks. In particular, dentists were still required to switch to a hypodermic needle to inject anesthetic once a hole was drilled with the small drill bit. This injection step is difficult because the opening produced by the small drill bit is often difficult to locate because it is covered by soft gingival tissue. Another problem with the Stabident system is that the stainless steel drill bits are not properly tempered. As a result of the this the drill bits occasionally wear out prematurely. Worn out drill bits generate excessive heat during use that may cause heat damage to the surrounding bone tissue. In addition, excessive heat levels occasionally cause melt-down and detachment of the plastic hub attached to the drill bit. This can result in the detached drill head being left inside the patient's jaw bone leading to further complications.

Rotary dental tools with hollow bits have been used in the past as a grinding tool. Such a tool has a low speed and relatively large-diameter hollow bit for grinding bone while supplying water to the grinding area to lubricate and flush particles. However, this art does not disclose a means to supply anesthetic or medication to a tooth.

SUMMARY OF THE INVENTION

In order to meet these concerns, the present invention is directed to an intraosseous and/or hard tissue drug delivery system that combines perforating and drug delivering functions in one device and one operation. The invention encompasses a medication injection device having a handle and a rotary drive mechanism, a hollow drill bit, and a fluid dispensing mechanism mounted in the handle and associated tubing to supply a medication fluid through the hollow drill bit to the patient.

In a preferred embodiment, the hollow drill bit of the medication injection device is a hypodermic needle having a sharpened point. Preferably, the fluid dispensing mechanism of the medication injection device includes a fluid reservoir, a duct extending between the fluid reservoir and the bore of the drill bit, a plunger slidably mounted and coupled to the fluid reservoir, and means for moving the plunger to supply fluid to the drill bit. The medication injection device also includes a drill motor for rotating the drill bit. The fluid dispensing means of this embodiment includes an injection gear motor and a drive mechanism coupled to the plunger and driven by the motor. In this embodiment, the means for moving the plunger further includes two limit switches that are electrically coupled to the injection gear motor and that open when contacted by the plunger to define the limits of travel of the plunger.

The invention preferably includes a foot control pedal operatively coupled to the drill. The foot control pedal includes a first switch electrically connected to the first motor and a second switch electrically connected to the second motor. The operator of the medication injection device controls the drilling and medication injection by positioning the foot control pedal.

An important feature of this embodiment is that the drill bit and duct can be detachable and disposable. In such an embodiment of the invention, the disposable medication dispensing device comprises a "transfuser" and a rotatable hollow drill bit mounted to the transfuser. The transfuser provides a duct or tubing to transfer medication fluid from the fluid dispenser to the hollow drill bit. The transfuser includes a detachable housing, and a duct extending through the housing between the fluid dispenser and the hollow drill bit.

The fluid reservoir of the medication injection device can be a removable cartridge containing medication fluid. When a cartridge is used, the duct of the transfuser preferably has a sharpened tip at a proximal end that engages a sealed end of the cartridge.

Another aspect of the invention is directed to a method of administering anesthetic or other medication to a tissue by drilling an opening in the tissue with a hollow drill bit and injecting the anesthetic or medication into the opening through the hollow drill bit. In this embodiment, the tissue to be drilled includes bone, cartilage and tendon. The step of injecting anesthetic or other medication can be performed before, during, and/or after the drilling step.

The invention is also directed to a method of administering medication to a tissue by a multistep process. In a first step, a drilling apparatus having a reservoir of medication, a hollow drill bit, means for rotating the drill bit, and a means for supplying the medication to the hollow drill bit is provided. Secondly, an opening is drilled in a tissue with the hollow drill bit. Thirdly, the medication is injected through the hollow drill bit and the drilled opening and into the tissue. The medication may be supplied through the hollow drill bit to the tissue before, during, or after the drilling step.

In other words, the invention is an intraosseous and/or hard tissue drug delivery system that combines perforating and drug delivering functions in one device and one operation. An advantage of the present invention is that it provides a comprehensive intraosseous drug delivery system that maximizes the efficiency of the intraosseous injection technique for dental and other potential medical applications. This system incorporates both the perforation and the injection steps into one continuous action without replacing the drill (or perforator) with an injection needle. This invention provides the solution to the problems of intraosseous injection encountered by dentists in dental anesthesia heretofore. This invention also provides broader applicability of the intraosseous injection technique in dental anesthesia and other medications.

The preferred embodiment of the invention is a dental drill that includes five basic parts: a hollow drill bit, a detachable transfuser, a dental-drill handpiece, a handle and a foot-control pedal. A hub of the hollow drill bit engages an adapter at a distal end of the transfuser. The hub of the drill bit can spin freely in the adapter of the transfuser. Stainless steel hypodermic tubing is embedded inside the transfuser with one end protruding into the center of the hub of the drill bit. The other end of the hypodermic tubing of the transfuser is sharpened and protrudes from a proximal end of the transfuser and penetrates a rubber cap of a drug or medication cartridge. The drill bit is driven in rotation by a DC motor and associated rotary couplings located in the handle. The handle also contains a drug cartridge chamber with a plunger, and a gearmotor that drives the plunger to inject the medication through the transfuser and out the end of the hollow drill bit. The footcontrol pedal contains a power supply and switches to control the drill motor and the medication dispenser gearmotor.

The hollow drill bit is preferably sized at about 27 G (gauge), so it will produce only a very small hole in the bone. It causes no significant tissue damage to the bone structure. Since the injection will start at the same time as the drilling, the continuous flow of medication through the core of the drill bit will facilitate the heat dispersion and also act as a lubricant to prohibit overheating of the drill. Therefore, the problems of earlier methods such as potential heat damage to the surrounding bone and the premature wearing of the drill can be avoided. The hardened drill bit with its sharp cutting angle provides a smooth drilling action, preventing the generation of excess heat.

The structure of the transfuser provides several functions: to transfer the drug solution from the cartridge to the hollow drill bit, and to anchor the drill bit and hypodermic tubing at a relatively fixed position to the dental handpiece and the handle. Furthermore, if the drill bit is designed to load from the back, the transfuser also backs up the drill bit to support it during the drilling and injection without leaking. At the drill bit adapter, the transfuser has a protruding hypodermic tubing that is precisely fitted into a center hole of the hub of the hollow drill bit. The diameter of the tubing is less than one thousandths of an inch smaller than the center hole. Sterilized petroleum jelly is used as a lubricant and a sealing material.

The handle contains a high-speed, high-torque motor that provides the drilling power. The type of the motor that can be used for this function includes, but is not limited to electric motors and air (or other fluid) turbine motors. The injection compartment contains a gear motor that controls the motion of the plunger of the injector. The moving range of the injector plunger is confined by two limit switches. An alternative design for this compartment accommodates an air pressure controlled plunger.

The foot control pedal controls the power on-off of the two motors and also gives variable speed adjustment to the injection plunger, plus a reverse motion switch for the plunger.

Before this invention, intraosseous injection techniques in dental anesthesia encountered major difficulties for both patients and dentists. During the early development stage of intraosseous injection, the drill bits would cause tremendous bone damage to the patient and create a greater chance of inflammation and infection. At a later stage, a special drill bit was developed, but its two-step operation makes it difficult for dentists to find the hole under the gum tissue. It also had the problem of mismatching the hole and needle by size. Further, the usefulness of the device is generally limited to the front teeth, because the limited space and angle make the application to the back teeth much more difficult. Only the present invention has eliminated these problems. Because of the single step action, the present invention avoids the mismatching problem, which allows the technique to be used throughout the mouth. Also, the fine drill bit will not produce significant bone damage.

This invention is not limited to injecting oral anesthetic in dental applications. The invention is broadly usable for injecting a wide range of medications, including antibiotics, and in other medical and veterinary applications.

The features and advantages described in the specification are not all inclusive, and particularly, many additional features and advantages will be apparent to one of ordinary skill in the art in view of the drawings, specification and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

DETAILED DESCRIPTION OF THE PREFERRED EMBODIMENTS

FIGS. 1 through 22 of the drawings depict various preferred embodiments of the present invention for purposes of illustration only. One skilled in the art will readily recognize from the following discussion that alternative embodiments of the structures and methods illustrated herein may be employed without departing from the principles of the invention described herein.

One aspect of the present invention is a medication injection device having a hollow drill bit and means for injecting medication through the hollow drill bit. The preferred embodiment of the device is a dental drill, as shown in FIGS. 1A–1D and designated in its entirety by reference number 10. Dental drill 10 includes a hollow drill bit 12, a transfuser 14, a dental handpiece 16 and a handle 18. In addition, a foot control pedal 20 (FIG. 17) is connected electrically to the handle 18 and is used to control the operation of the dental drill. When assembled, the drill bit 12 is inserted into an adapter at a distal end of the transfuser 14 and that assembly is attached to the dental handpiece 16. The combined assembly is inserted into the handle 18 to connect the dental handpiece to a rotary drive mechanism, located in the handle, and to connect the transfuser 14 to a drug cartridge, also located in the handle.

A detailed description of the preferred embodiment is shown in FIGS. 2–17.

As shown in FIGS. 2–6, the transfuser 14 is mounted to the dental handpiece 16 and contains a duct or tubing 22 that extends between the hollow drill bit 12 and a fluid reservoir or drug cartridge 24. The transfuser 14 is preferably made of plastic material and is embedded with stainless steel hypodermic tubing 22. The stainless steel tubing is preferably 20 G.

Figure 3:
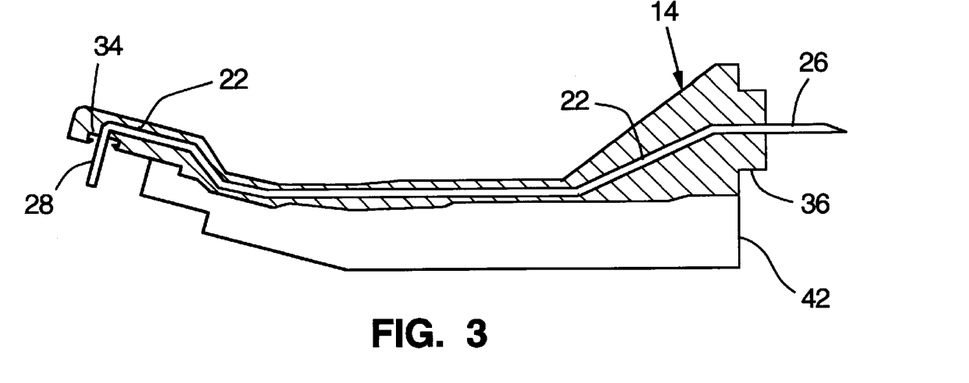
FIG. 3 is a longitudinal section of a transfuser, sometimes referred to as a disposable medication dispensing device, which is one component of the dental drill of the present invention.
Figure 4:
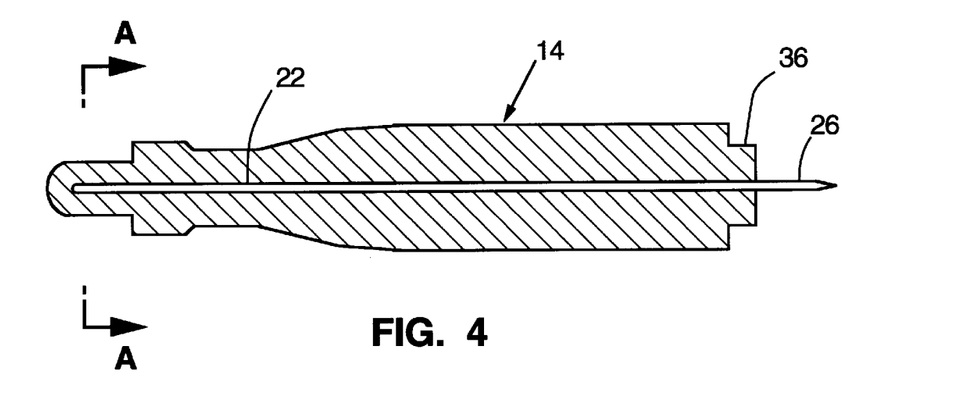
FIG. 4 is a top section of the transfuser of FIG. 3.
Figure 9:
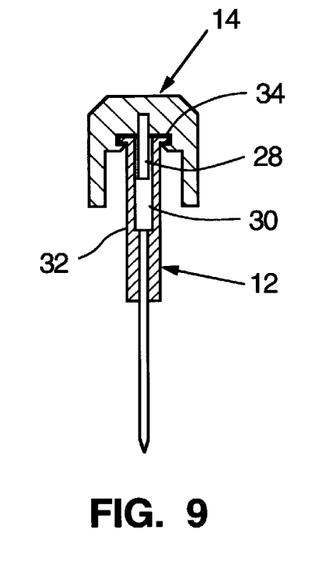
FIG. 9 is a sectional view of an adapter of the transfuser with the hollow drill bit attached.
Figure 10:
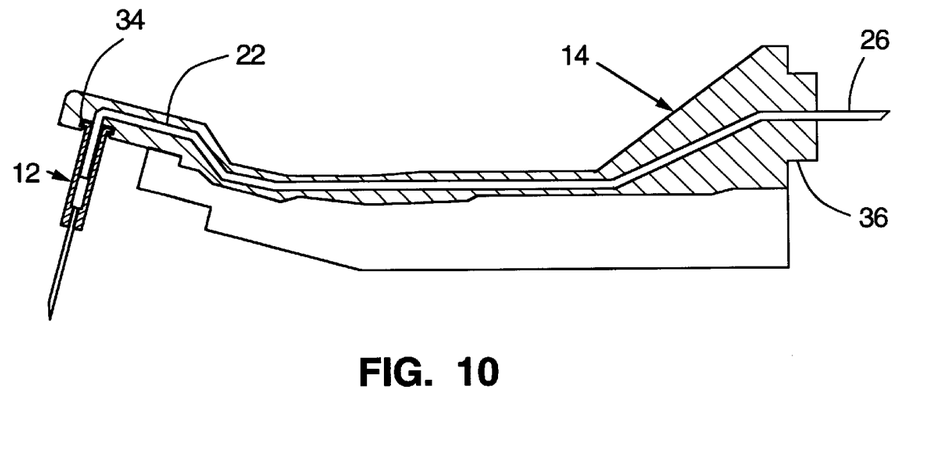
FIG. 10 is a longitudinal section of the transfuser assembled with the hollow drill bit.
Figure 11:
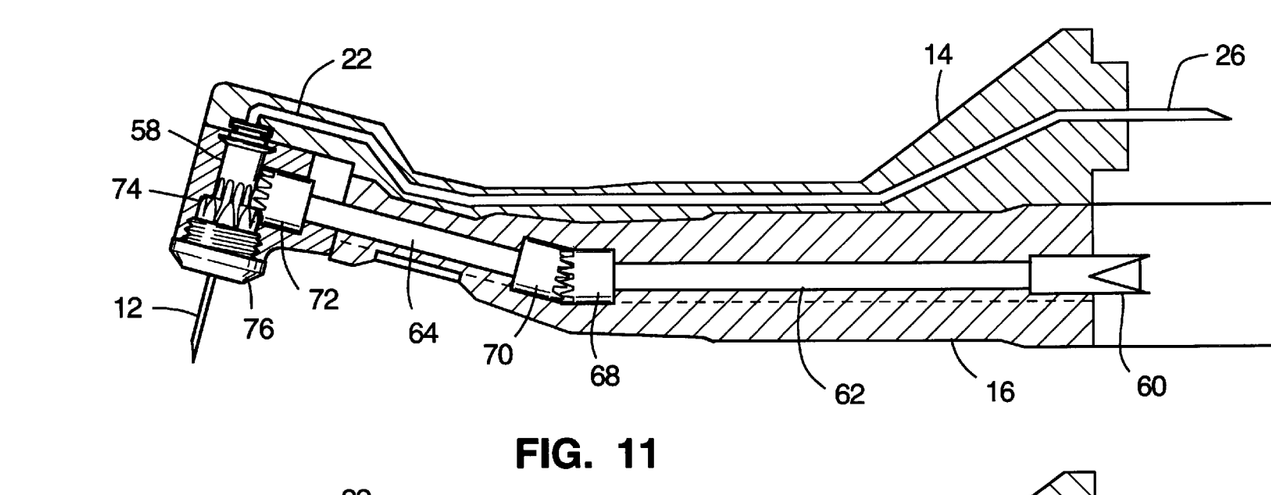
FIG. 11 is a view, partially in section, of the transfuser and drill bit as installed on a dental handpiece.
Figure 12:
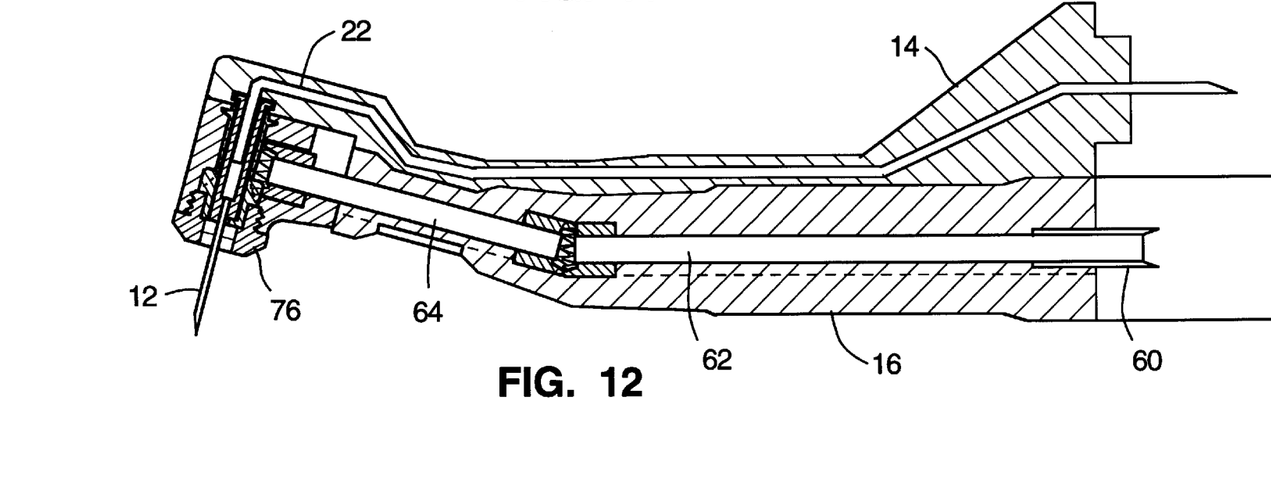
FIG. 12 is a sectional view of the transfuser and drill bit as installed on the handpiece.
Figure 13:
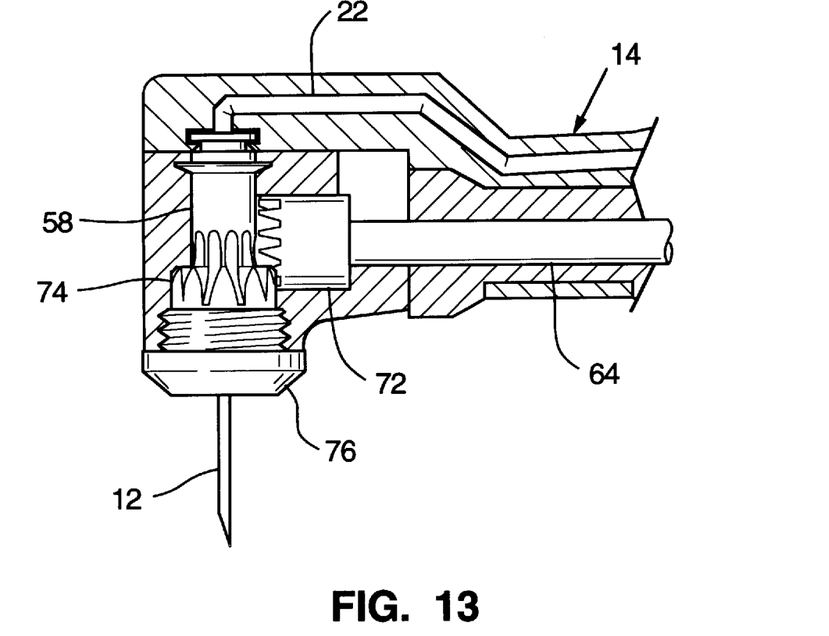
FIG. 13 is a view, partially in section, of a drill head of the handpiece.
Figure 14:
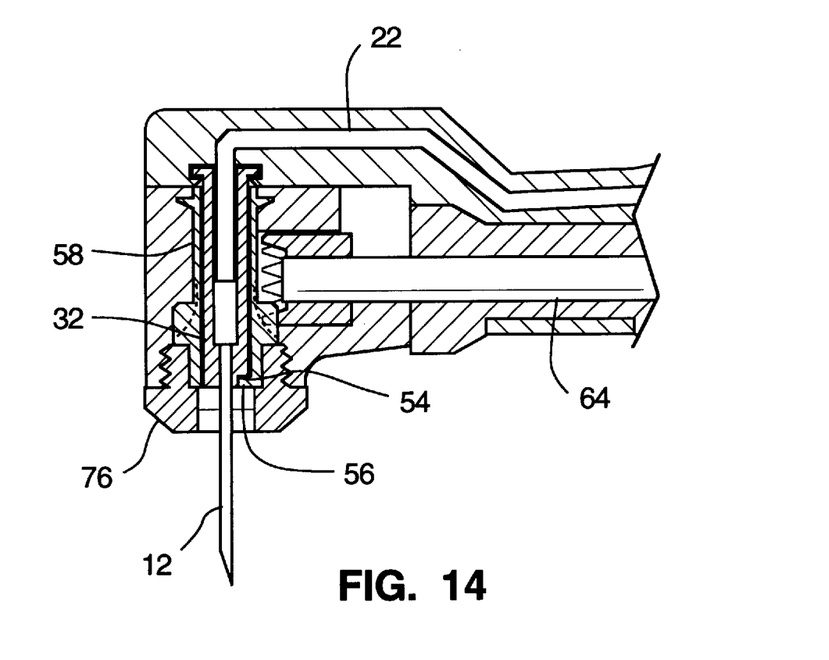
FIG. 14 is a sectional view of the drill head of FIG. 13.
Figure 15A:
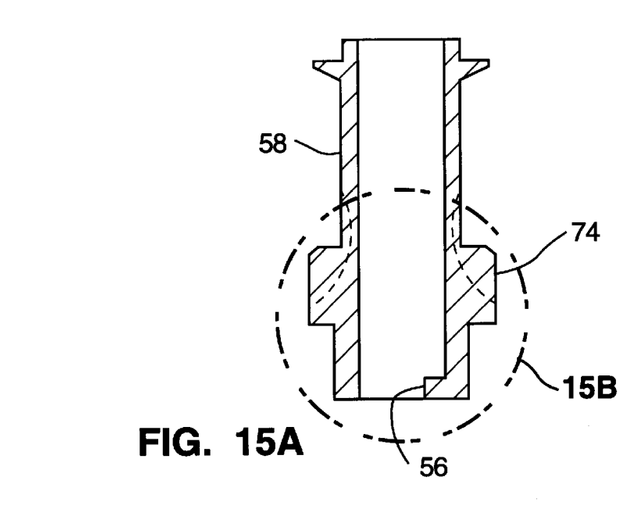
FIG. 15 is a longitudinal section and a partial perspective view of a spindle core.
Figure 15B:
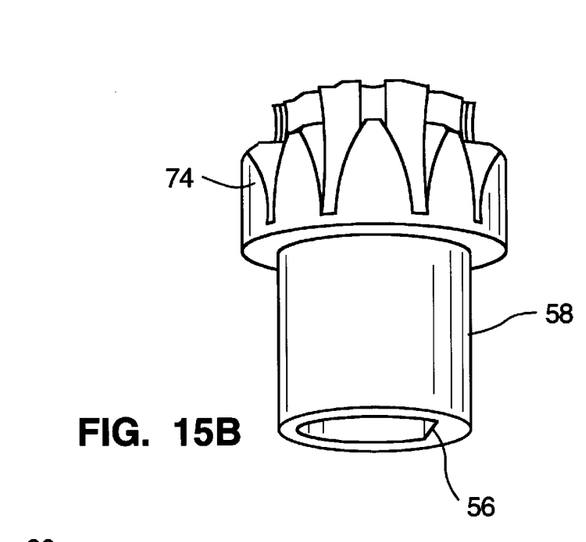

The tubing 22 within the transfuser 14 has a proximal end 26 and a distal end 28. As shown in FIG. 3, the distal and proximal ends of the tubing protrude to the outside of the transfuser 14. The distal end 28 of the tubing is blunt-ended and adapted to fit into a central bore 30 of a hub 32 of the hollow drill bit 12. (FIGS. 9 and 10). The distal end of the transfuser 14 has an adapter 34 that receives and clamps onto the drill bit 12.

Figures 1A, 1B:
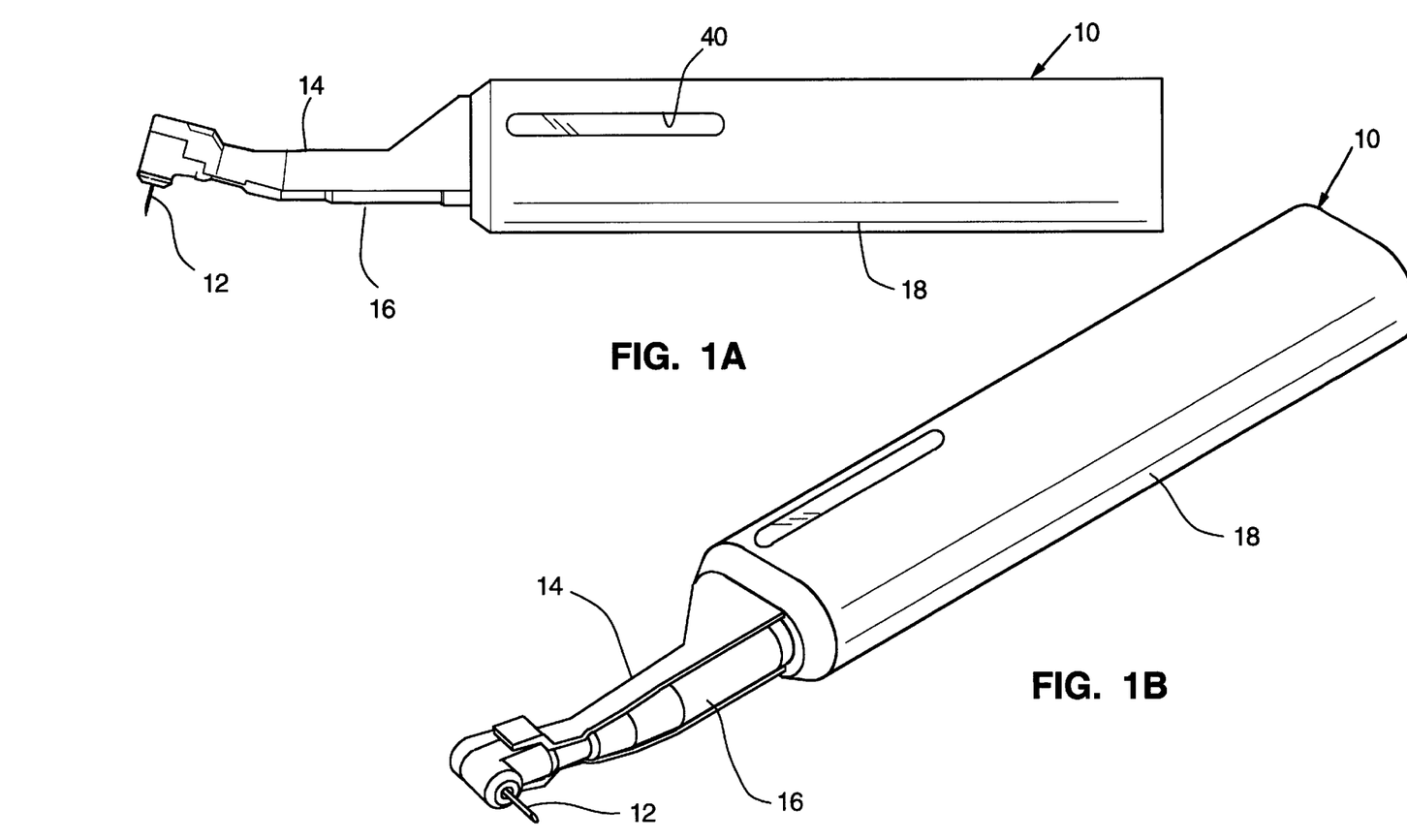
FIGS. 1(a) and 1(b) show the dental drill of the invention in a fully assembled state.
Figure 1C:
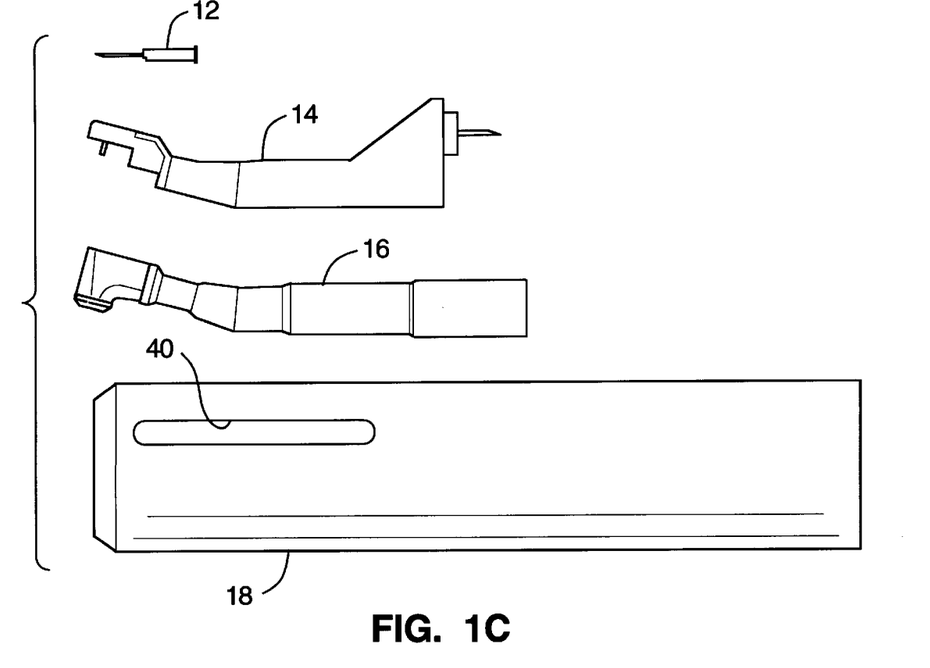
FIGS. 1(c) and 1(d) are exploded views of the dental drill showing its four major parts.
Figure 1D:
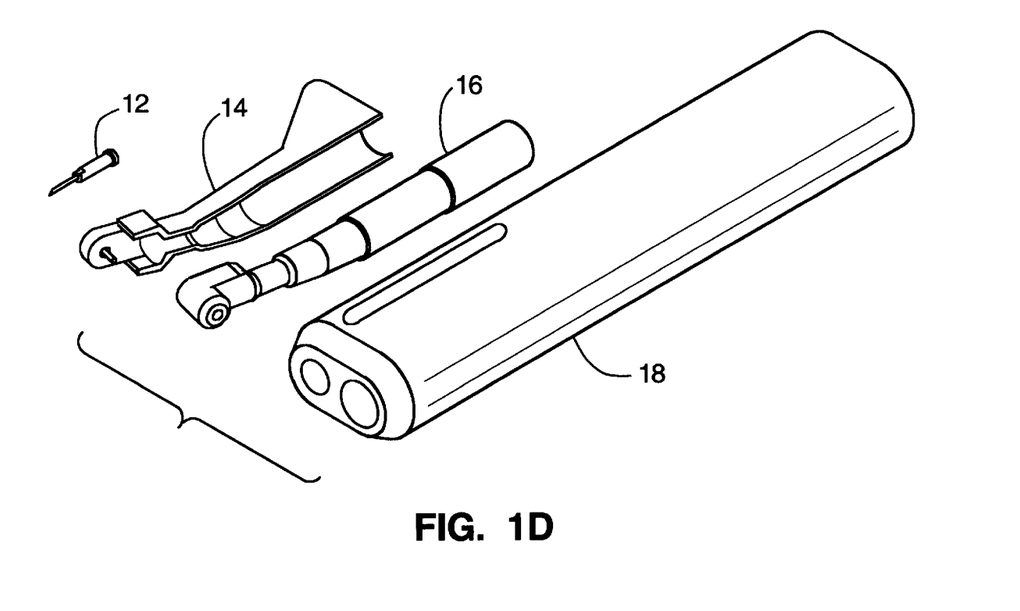
Figure 2:
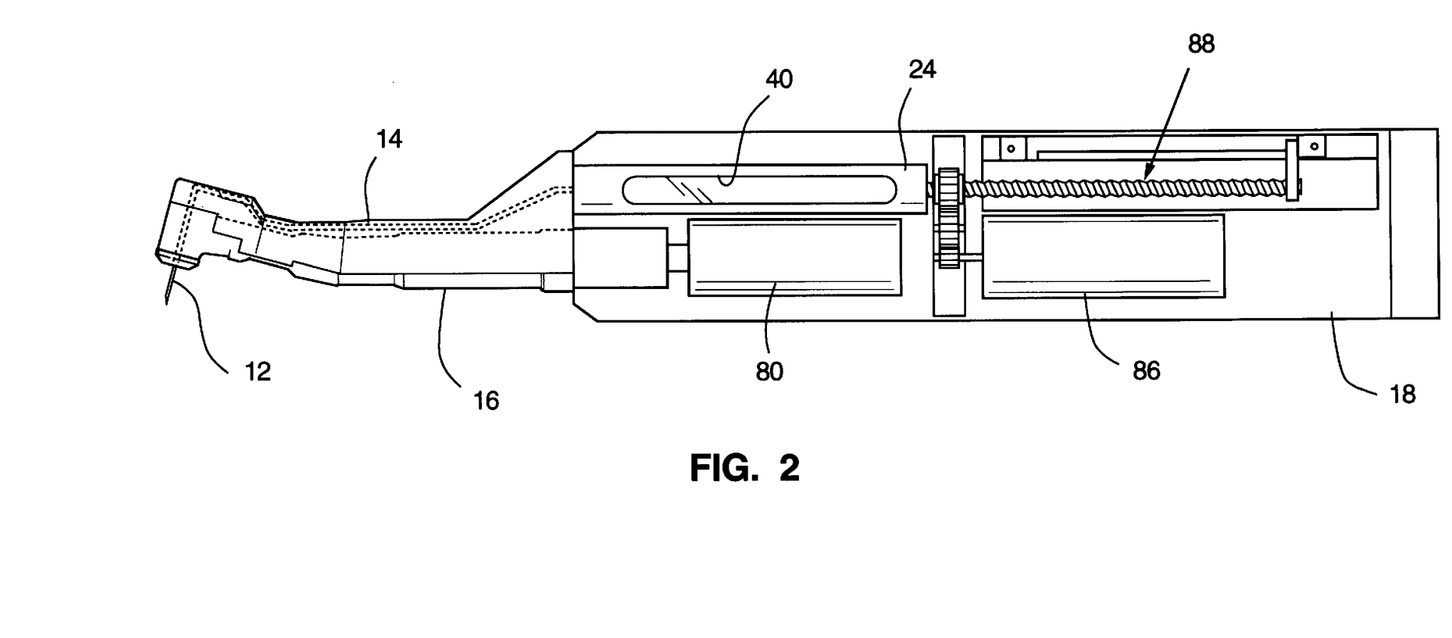
FIG. 2 is a cut-away side view of the dental drill and illustrates its internal structural arrangement.
Figure 16:
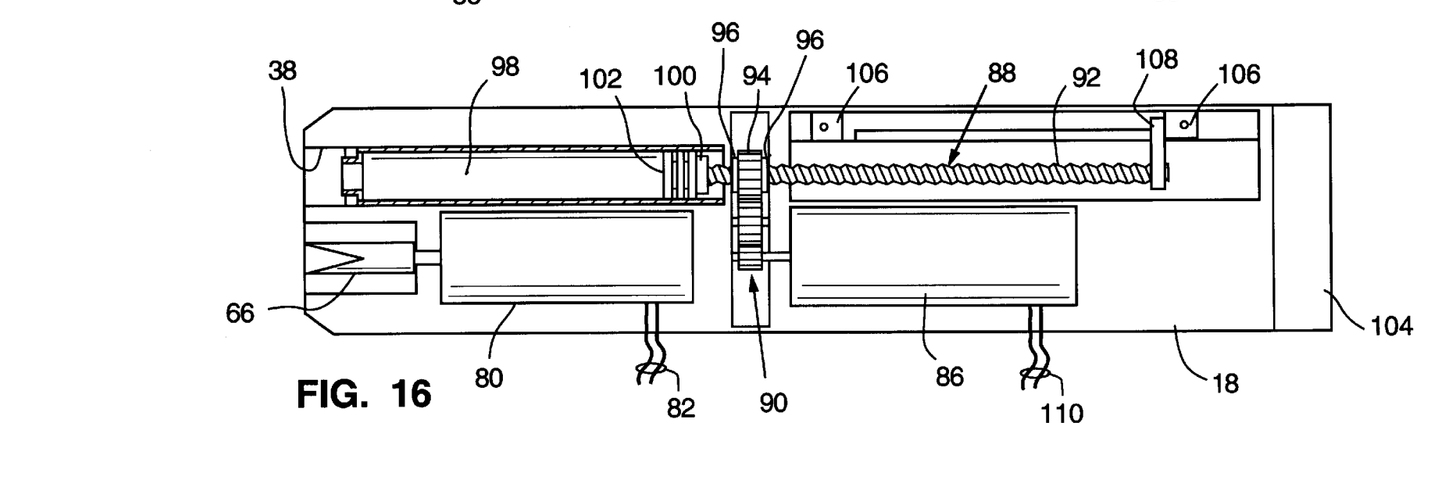
FIG. 16 is a sectional view of a handle of the dental drill of the present invention.

The proximal end 26 of the tubing 22 has a sharpened tip that protrudes from the center of a circular disk 36 (see FIG. 3). When the transfuser 14 is mounted on the handle 18, the disk 36 of the transfuser fits into a receiving bore 38 in the handle (FIG. 16). In that position, the sharpened tip of the tubing is aligned with the center of a fluid reservoir or drug cartridge 24 (FIGS. 2, 16). The fluid reservoir 24 preferably is a drug cartridge with a rubber sealant cap which is penetrated by the sharpened proximal end 26 of the tubing 22. A viewing window 40 in the handle 18 allows the operator to monitor the contents of the cartridge 24.

Figures 5, 6:
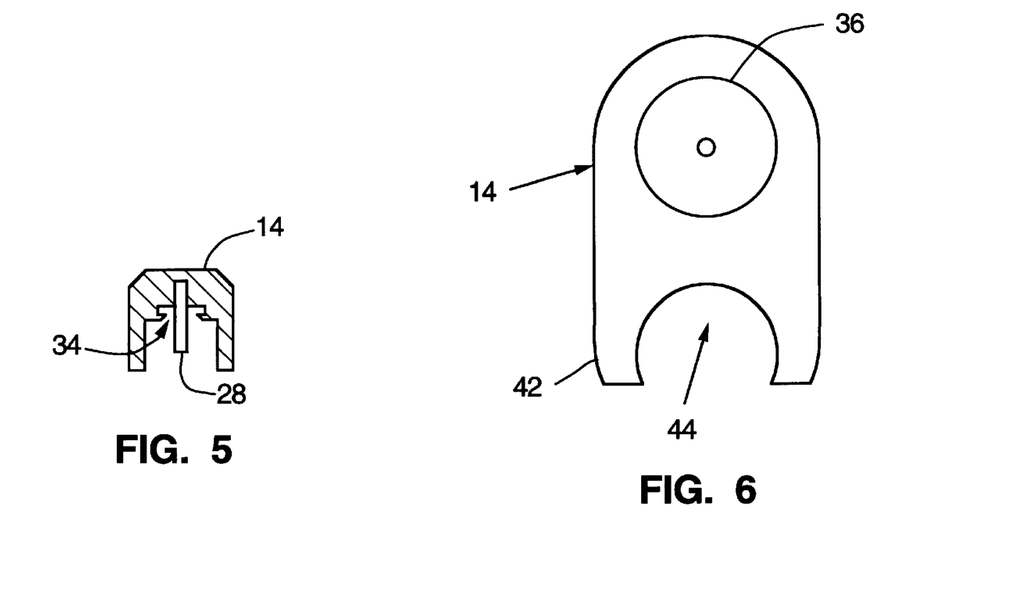
FIG. 5 is a cross section view of a head portion of the transfuser, as taken alone section line A—A in FIG. 4.
FIG. 6 is a view of a distal end of the transfuser.

As best shown in FIG. 6, the transfuser 14 includes two side wings 42 that form a open cavity 110 sized according to the outer dimension of the dental handpiece 16. When the transfuser is mounted on the dental handpiece 16, the side wings 42 engage and clamp to the body of the dental handpiece.

Figure 7:
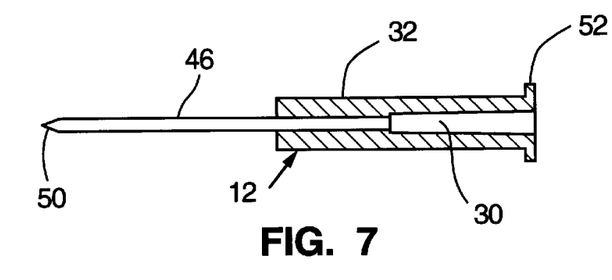
FIG. 7 is a longitudinal section of a hollow drill bit and associated hub used with the dental drill of the present invention.
Figure 8:
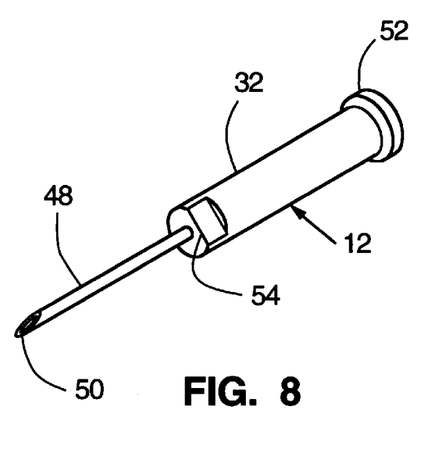
FIG. 8 is a perspective view image of the hollow drill bit and hub.

As shown in FIGS. 7–8, the hollow drill bit 12 is composed of a stainless steel needle 46 and a metal or plastic hub 32. The needle is preferably 27 G (0.016 inch diameter), but may range from 22 G to 36 G (0.028 to 0.00425 inch diameter, respectively). The needle 46 has a sharpened tip 50. The hub 32 is cylindrical in shape with a flange 52 at the end opposite the tip 50. The flange 52 engages the adapter 34 of the transfuser 14 to hold the drill bit, as shown in FIGS. 9–10. Once assembled, the drill bit is held by the adaptor 34 and cannot be separated from the transfuser 14 without damaging the device. Since the transfuser 14 and drill bit 12 are intended to be disposable as a unit, this construction prevents accidental reuse of contaminated biological materials. The distal end of the tubing 22 engages the central bore 30 of the hub 32 of the drill bit 12. Sterilized petroleum provides a lubricant and seal between the tubing 22 and the hub 32 of the drill bit, which permits the drill bit to rotate within the adapter 34, yet ensures that medication supplied from the tubing 22 does not leak out. The hub 32 of the drill bit includes a flat 54 that engages a corresponding retainer 56 of a spindle 58 of the handpiece 16 (FIG. 14), which provides a positive rotational engagement between the spindle and the drill bit.

As shown in FIGS. 11–15, the dental handpiece 16 is similar to a standard low speed dental handpiece with one variation: a retainer plate 56 of the handpiece is located on the needle side rather than the back side of the handpiece in order to accommodate rear-loading of the drill into the handpiece. The handpiece 16 includes two shafts 62, 64 that transmit rotary motion from a motor in the handle 18 to the drill bit 12. Shaft 62 has a coupling 60 at a proximal end of the shaft that engages a mating coupling 66 (FIG. 16) in the handle 18. On the distal end of shaft 62 is a gear 68 that engages a mating gear 70 on the proximal end of shaft 64. The distal end of shaft 64 has a gear 72 that engages a gear 74 on the spindle 58 and drives it in rotation. The spindle 58 is retained in the handpiece by a cap 76 that screws into the handpiece. The drill bit 12 is inserted into the spindle 58 from the rear, with the flat 54 on the hub 32 aligned with the retainer 56 inside the spindle 58. After the drill bit is inserted into the spindle, the transfuser 14 can be attached.

The handle 18 is illustrated in FIG. 16. The handle 18 contains a drill motor 80 that directly drives coupling 66 and through that coupling and the associated shafts and gears of the handpiece 16 drives the drive bit 12 in rotation. The drill motor 80 is electrically connected through wires 82 to a switch 84 in the foot control pedal 20 (FIG. 17), which electrically turns the drill motor on and off. The drill motor may be a DC motor with output speed of 15,000 to 20,000 rpm. Alternatively, the drill motor may be an air or water (or other fluid) turbine.

The handle 18 also contains a gear motor 86 that drives a plunger assembly 88 through a reduction gear train 90. The plunger assembly 88 includes a threaded rod 92 that passes through the center and engages an internally threaded output gear 94 of the gear train 90. The threaded rod 92 translates linearly when the gear train 90 rotates. The gear train further includes two thrust washers 96 that longitudinally restrain the output gear 94.

The threaded rod extends into a drug cartridge compartment 98. The distal end of the plunger has a disc-shaped plate 100 and a tip 102 that are slightly smaller in diameter than the inner diameter of a drug cartridge. When the drug cartridge is installed in the compartment 98, the distal tip 102 of the plunger fits inside the cartridge. When the gear motor rotates, the gear train 90 causes the plunger to move distally, which pushes fluid from the cartridge holder into the proximal end of the tubing 22.

The drug cartridge compartment 98 has a viewing window 40 (FIG. 2) that allows the operator to monitor the dispensing of the medication. The proximal end of the handle 18 includes an end-cap 104.

The plunger assembly 88 further contains a two snap-action limit switches 106 and a plate 108. The plate 108 is mounted to the proximal end of the threaded rod 92 and prevents the rod from rotating. The plate 108 contacts the limit switches 106 at the limits of travel of the plunger assembly. The gear motor 86 is electrically connected through wires 110 to the foot control pedal 20 (FIG. 17) so that the operator can control the direction and speed of the plunger. The limit switches 106 are also electrically connected to the foot control pedal 20.

Instead of a mechanically driven plunger, the function of dispensing the medication fluid could be accomplished with a pressure-driven device.

Figure 17:
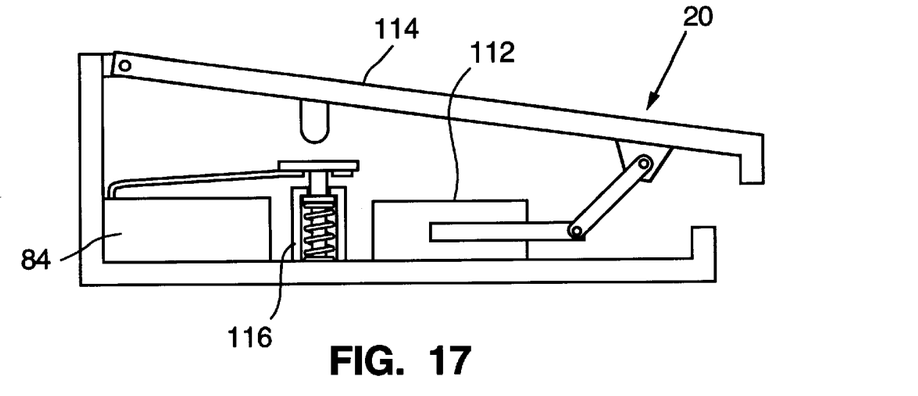
FIG. 17 is a sectional view of a foot pedal used to control the dental drill.

Both the drill motor 80 and the gear motor 86 are controlled by the foot control pedal 20, shown in FIG. 17. The foot control pedal 20 contains two switches 84, 112 in cascade-arranged position. One switch 112 controls the power for the plunger gear motor 86, while the other switch 84 controls the power for the drill motor 80. The foot control pedal 20 includes a hinged cover plate 114 that is spring-loaded upward by a spring 116. When the operator pushed down on the cover plate 114, switch 112 turns on the plunger gear motor 86, which begins to supply medication to the drill bit. The anesthetic fluid can be thus used to initially numb the drilling site before drilling. Then, by pushing down farther on the cover plate 114, the switch 84 is triggered, which turns on the drill motor and causes the drill bit to rotate at high speed, while at the same time the switch 112 continues to be triggered so that the medication continues to flow. When the operator wishes to stop drilling, the cover plate is allowed to raise up part way, to open the switch 84, while still depressing switch 112 and dispensing the medication. Finally, the operator can stop the flow of medication by removing pressure from the cover plate 114.

Figure 18:
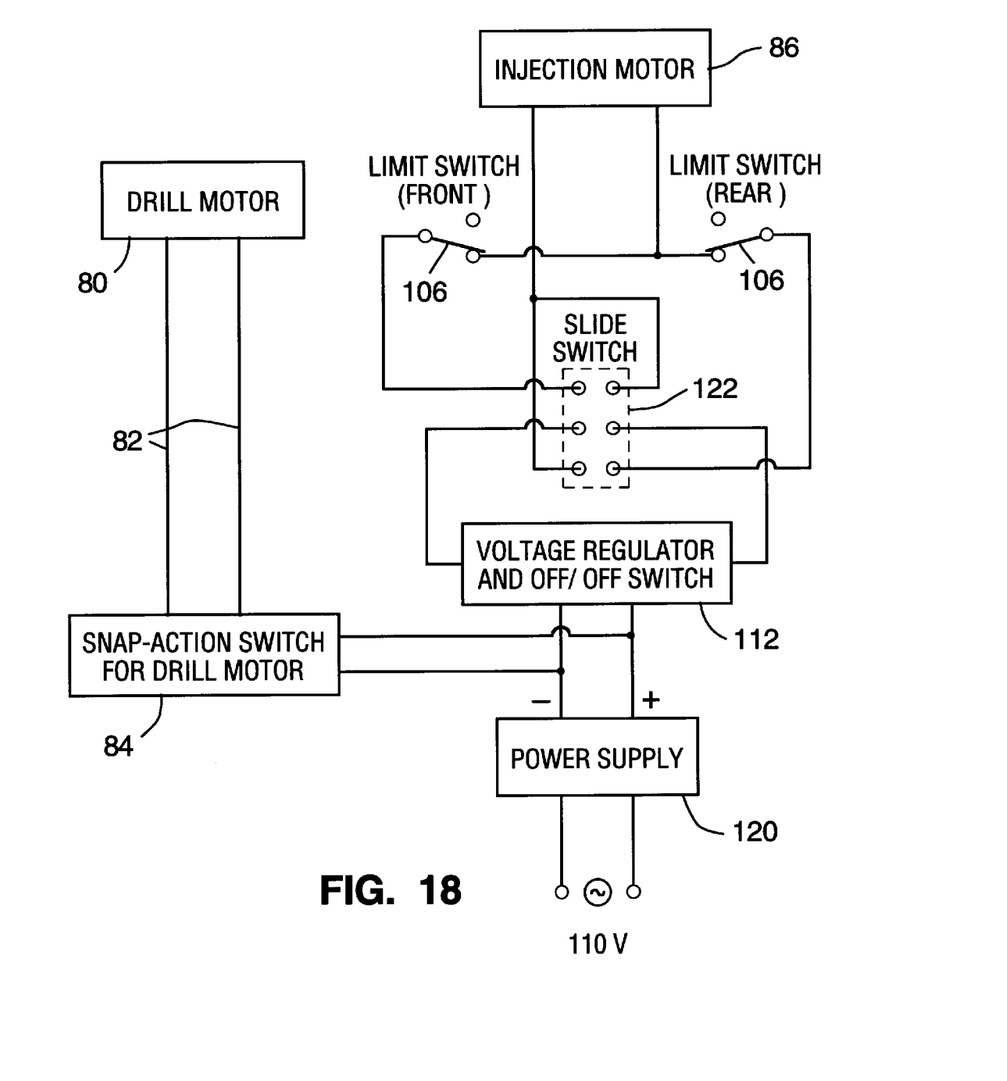
FIG. 18 is a block diagram of a circuit used in the dental drill of the present invention.
Figure 19:
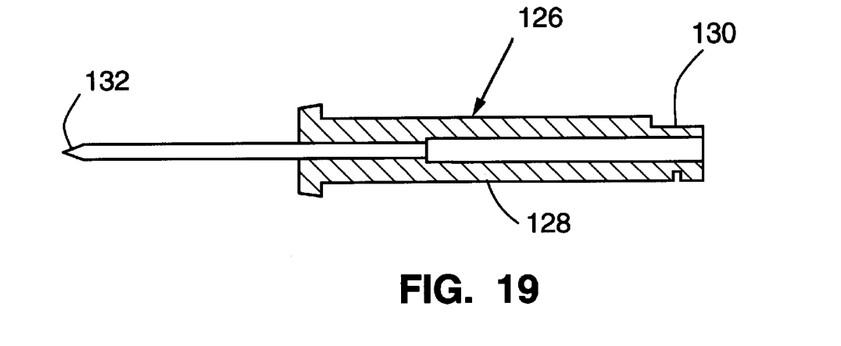
FIG. 19 is a longitudinal section of an alternative, front-loading drill bit.
Figure 20:
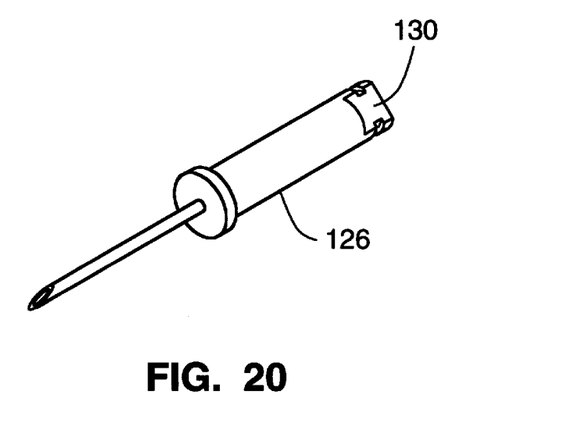
FIG. 20 is a perspective view of the front-loading drill bit.
Figure 21:
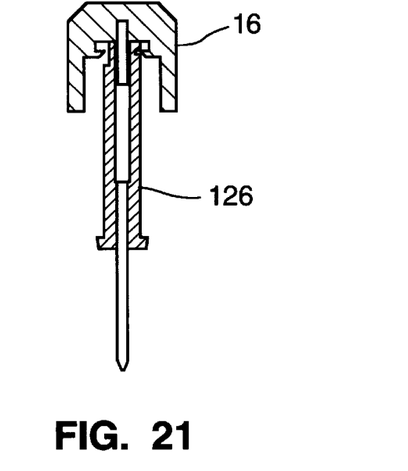
FIG. 21 is a sectional view of the front-loading drill bit as installed in the adapter of the transfuser.
Figure 22:
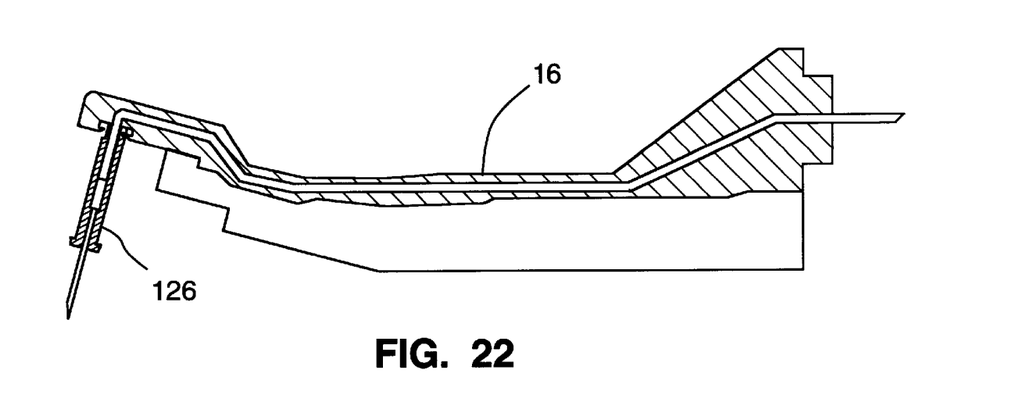
FIG. 22 is a longitudinal section of the transfuser and front-loading drill bit assembly.

The control circuitry of the invention is shown in FIG. 18. In addition to the switches 84 and 112, the foot control pedal 20 also contains a power supply 120 that converts AC to low-voltage DC. The switch 84 is simply connected in series between the power supply DC outputs and the drill motor 80. The wiring for the gear motor 86 is more complex. The switch 112 is a voltage regulator that is connected to the DC outputs of the power supply and outputs a variable voltage. The output of the voltage regulator 112 is input to the center terminals of a double-pole double-throw slide switch 122. The position of the slide switch determines the direction of motion of the plunger assembly 88. When the slide of the slide switch 122 is positioned at one extreme, the gear motor 86 is driven in one direction until a limit switch 106 is opened by contact by the plate 108. Then, the slide must be repositioned to the other extreme, which permits the gear motor 86 to operate in reverse until the other limit switch 106 is contacted.

In an alternative embodiment, shown in FIGS. 19–22, the hollow drill bit 126 is designed for front-loading. In this embodiment, the cylindrical hub 128 has a flat surface 130 at the end opposite the tip 132 of the drill bit. The flat surface 130 engages the spindle of the dental handpiece to hold the hub in place. This permits front-loading of the hollow drill bit 126.

To assemble the dental drill, the hollow drill bit is loaded onto the core of the spindle of the dental handpiece, either from the rear or the front, depending on the design. The transfuser 14 is then snapped on the top of the dental handpiece 16 so that the distal end 28 of the tubing 22 is positioned within the center bore of the hub of the drill bit. The distal end of the transfuser 14 is then pushed down to snap the hub of the drill bit into the adaptor of the transfuser 14. A drug cartridge is loaded into the cartridge compartment in the handle 18. After assembling the transfuser, the drill bit, and the dental handpiece, the disk 36 of the transfuser is matched with the drug cartridge holder to align the transfuser with the dental handpiece and the handle.

Once the dental drill 10 is assembled and the drug cartridge is in place, the operator can use it to deliver anesthetic, drugs, medication, or other fluids into or through hard tissue, such as, but not limited to, bone, cartilage, tendon, etc. The applicable field includes, but is not necessarily limited to, dental, medical and veterinary medicine. The medication or other fluid can be delivered before, during, and after drilling.

Since the hollow drill design provides continuity of drilling and injection, this device has many advantages over all other existing devices. In comparison to the rosehead bur or reamer, this device will only drill a hole slightly larger than an ordinary 27 G needle. Therefore, bone and tissue damage due to drilling is significantly reduced. In comparison to the perforator used in the Stabident System, this device allows the dentist to perform the injection before, during and/or after the drilling. Therefore, there is no separate needle and syringe needed. Second, because the drill and the needle are one and the same, there is no need to remove the drill and then to search for the tiny hole under the gum tissue with the equally small size needle, thereby eliminating a potential mismatch in sizes between the needle and the hole. Third, because of the continuous flow of liquid through the drill, it will serve both as a coolant and a lubricant to reduce the potential heat damage to the surrounding bone during the drilling process. Fourth, because of the cooling effect, the drill tip will remain sharp much longer.

In order to avoid contamination among patients, the drill bit and transfuser are intended to be disposable. Once the operator is finished using the device with one patient, the drill bit and transfuser are removed, the empty drug cartridge is removed, and the plunger is retracted. The device is readied for another patient by repeating the procedure described above, by loading another drill bit into the handpiece, placing another transfuser onto the handpiece, loading another drug cartridge into the handle, and then affixing the handpiece/transfuser assembly onto the handle. The device is then ready to be used with a new, sterile drill bit.

While the invention has been disclosed with reference to drilling holes in teeth, those skilled in the art will recognize that the invention will be useful for any procedure requiring the drilling of an opening and the delivery of fluid into tissue. From the above description, it will be apparent that the invention disclosed herein provides a novel and advantageous medication injection device and associated method. The foregoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

What is claimed is:

1. A medication injection device comprising:
   a housing for grasping by an operator, wherein the housing has a distal end;
   a rotatable hollow drill bit mounted to the distal end of the housing, wherein the drill bit includes a bore therethrough, and wherein the drill bit is suitable for intraosseous drilling;
   means disposed in the housing for rotating the drill bit; and fluid dispensing means including a fluid reservoir stationarily mounted in the housing and means for supplying a controlled dose of medication fluid for intraossaous injection through the bore of the drill bit.

2. A device as recited in claim 1 wherein the fluid dispensing means supplies the medication fluid to the bore of the drill bit while the drill bit is rotating.

3. A medication injection device comprising:

a housing for grasping by an operator, wherein the housing has a distal end;

a rotatable hollow drill bit mounted to the distal end of the housing, wherein the drill bit includes a bore therethrough;

means disposed in the housing for rotating the drill bit; and fluid dispensing means including a fluid reservoir stationarily mounted in the housing for supplying a medication fluid to the bore of the drill bit;

wherein the hollow drill bit includes a hypodermic needle having a sharpened point.

4. A medication injection device comprising:

a housing for grasping by an operator, wherein the housing has a distal end;

a rotatable hollow drill bit mounted to the distal end of the housing, wherein the drill bit includes a bore therethrough;

means disposed in the housing for rotating the drill bit; and fluid dispensing means including a fluid reservoir stationarily mounted in the housing for supplying a medication fluid to the bore of the drill bit;

wherein the means for rotating the drill bit includes a first motor coupled to the drill bit.

5. A medication injection device comprising:

a housing for grasping by an operator, wherein the housing has a distal end;

a rotatable hollow drill bit mounted to the distal end of the housing, wherein the drill bit includes a bore therethrough;

means disposed in the housing for rotating the drill bit; and fluid dispensing means including a fluid reservoir stationarily mounted in the housing for supplying a medication fluid to the bore of the drill bit, wherein the fluid dispensing means further includes a duct extending between the fluid reservoir and the bore of the drill bit, a plunger slidably mounted and coupled to the fluid reservoir, and means for moving the plunger to supply fluid to the drill bit.

6. A device as recited in claim 5 wherein the means for moving the plunger includes a second motor and a drive mechanism coupled to the plunger and driven by the motor.

7. A device as recited in claim 6 wherein the means for moving the plunger further includes two limit switches each disposed at a limit of travel of the plunger and electrically coupled to the second motor, wherein the limit switches are operable for opening when contacted by the plunger to define the limits of travel of the plunger.

8. A device as recited in claim 6, further including a foot control pedal operatively coupled to the drill and including a first switch electrically connected to the first motor and a second switch electrically connected to the second motor.

9. A device as recited in claim 5 wherein the drill bit and duct are mounted to a structure that is detachable, and wherein the detachable structure includes a clip that releasably attaches the detachable structure to the housing.

10. A device as recited in claim 5 wherein the fluid reservoir is a removable cartridge containing the medication fluid.

11. A disposable medication dispensing device adapted for use with a dental drill, wherein the dental drill has a drill motor and a coupling for rotating a drill bit, and wherein the dental drill further has a fluid dispenser containing medication fluid, the disposable device comprising:

a detachable housing including means for releasably attaching the housing to the dental drill;

a rotatable hollow drill bit mounted to the housing; and a duct extending through the housing between the fluid dispenser and the hollow drill bit.

12. A device as recited in claim 11 wherein the means for releasably attaching the housing includes a clip that engages the dental drill.

13. A device as recited in claim 11 wherein the hollow drill bit is a hypodermic needle having a sharpened point.

14. A device as recited in claim 11 wherein the duct includes a sharpened tip at a proximal end thereof, and wherein the sharpened tip engages the fluid dispenser when the device is attached to the dental drill.

15. A device as recited in claim 11 wherein the duct includes a blunt tip at a distal end thereof, and wherein the blunt tip fits within a bore of the hollow drill bit.

16. A method of administering medication to a tissue, said method comprising the steps of:

drilling an opening in said tissue with a hollow drill bit;

injecting medication into said opening through the hollow drill bit while drilling; and further injecting medication into said opening through the hollow drill bit after the step of drilling has been completed.

17. A method as recited in claim 16 wherein said tissue is selected from the group comprising bone, cartilage and tendon.

18. A method as recited in claim 16 wherein the medication is an oral anesthetic.

19. A method as recited in claim 16 wherein the step of injecting medication is also performed before the step of drilling.

20. A method of administering a medication comprising the steps of:

providing a drilling apparatus having a reservoir of the medication, having a hollow drill bit and means for rotating the drill bit, and having a means for supplying the medication to the hollow drill bit;

drilling an opening in a tissue with the hollow drill bit and injecting medication through the hollow drill bit while drilling; and injecting the medication through the hollow drill bit and the drilled opening into the tissue after the drilling step has been completed.

* * * * *